(12) United States Patent
Suzuki et al.

(10) Patent No.: US 8,067,648 B2
(45) Date of Patent: Nov. 29, 2011

(54) METHOD FOR SYNTHESIZING RADIOACTIVE LIGAND HAVING $^{18}$F-LABELED FLUOROBENZENE RING

(75) Inventors: Kazutoshi Suzuki, Chiba (JP); Ming-Rong Zhang, Chiba (JP); Katsushi Kumata, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 674 days.

(21) Appl. No.: 12/161,974

(22) PCT Filed: Nov. 29, 2006

(86) PCT No.: PCT/JP2006/323805
§ 371 (c)(1),
(2), (4) Date: Jul. 24, 2008

(87) PCT Pub. No.: WO2007/088670
PCT Pub. Date: Aug. 9, 2007

(65) Prior Publication Data
US 2009/0069592 A1 Mar. 12, 2009

(30) Foreign Application Priority Data

Jan. 31, 2006 (JP) ................................ 2006-021967

(51) Int. Cl.
*C07B 59/00* (2006.01)
*C07C 231/12* (2006.01)
*C07C 233/25* (2006.01)
*C07C 303/26* (2006.01)
*C07C 309/73* (2006.01)

(52) U.S. Cl. ........ 570/147; 570/127; 570/143; 564/218; 562/828; 436/126

(58) Field of Classification Search ................ None
See application file for complete search history.

(56) References Cited

U.S. PATENT DOCUMENTS 4,513,137 A * 4/1985 Koser et al. ............ 546/14
5,073,643 A 12/1991 Crivello

FOREIGN PATENT DOCUMENTS

JP 2004-298802 A 10/2004

OTHER PUBLICATIONS

Database CAPLUS on STN, Acc. No. 1997:118371, Wirth et al., Tetrahedron: Asymmetry (1997), 8(1), p. 23-26 (abstract).*
Database CAPLUS on STN, Acc. No. 1996:367725, Kang et al., Journal of Organic Chemistry (1996), 61(14), p. 4720-4724 (abstract).*
Database CAPLUS on STN, Acc. No. 1991:408158, Ochiai et al., Tetrahedron Letters (1991), 32(10), p. 1327-1328 (abstract).*
Database CAPLUS on STN, Acc. No. 1987:533959, Zhu et al., Gaodeng Xuexiao Huaxue Xuebao (1986), 7(3), p. 233-238 (abstract).*
Database CAPLU on STN, Acc. No. 2003:1008605, Cao et al., Jingxi Huagong Zhongjianti (2003), 33(1), p. 36-37 (abstract).*
Database CAPLUS on STN, Acc. No. 1985:453793, Koser et al., US 4513137 (Apr. 23, 1985) (abstract).*
Victor W. Pike, et al., "Facile synthesis of substituted diaryliodonium tosylates by treatment of aryltributylstannanes with Koser's reagent", J. Chem. Soc., Perkin Trans., 1999, pp. 245-248, No. 3.
Carol S. Carman, et al., "Regiospecific Synthesis of Aryl (2-furyl) iodonium Tosylates, a New Class of Iodonium Salts, from [Hydroxy (tosyloxy) iodo] arenes and 2-(Trimethylsilyl) furans in Organic Solvent", J. Org. Chem., 1983, pp. 2534-2539, vol. 48, No. 15.
Sandrine Langle, et al., "General access to para-substituted styrenes", Journal of Organometallic Chemistry, 2003, pp. 113-119, vol. 671.
Frank R. Wust, et al., "Synthesis of 4-[$^{18}$F] fluoroiodobenzene and its application in sonogashira cross-coupling reactions", J. Label. Compd. Radiopharm., 2003, pp. 699-713, vol. 46, No. 8.
Victor W. Pike, et al., "Reactions of Cyclotron-produced [$^{18}$F] Fluoride with Diaryliodonium Salts-a Novel Single-step Route to No-carrier-added [$^{18}$F] Fluoroarenes", J. Chem. Soc. Commun., 1995, pp. 2215-2216, No. 21.
Ming-Rong Zhang, et al., Practical Method for Synthesizing [$^{18}$F]-Fluorobenzene by Nucleophilic Substitution Reaction of [$^{18}$F]-Fluorine, 45$^{th}$ General Meeting of the Japanese Society of Nuclear Medicine, Sep. 2005, p. 363.

* cited by examiner

*Primary Examiner* — Brian J Davis
(74) *Attorney, Agent, or Firm* — Sughrue Mion, PLLC

(57) ABSTRACT

A phenyl tin compound is synthesized by using a derivative having various functional groups and a bromo- or iodo-benzene ring as a labeling material of a radioactive ligand. On the other hand, a novel hydroxytosyl iodobenzene compound having an electron-donating group is obtained by oxidizing iodobenzene having one or more electron-donating groups and reacting it with tosylic acid. Then, a diphenyliodonium salt which is a labeling precursor is synthesized by reacting the resulting compound with various phenyl tin compounds. Finally, a $^{18}$F-labeled ligand having various functional groups and a [$^{18}$F] fluorobenzene ring is synthesized by reacting the resulting diphenyliodonium salt with [$^{18}$F]F$^-$.

14 Claims, No Drawings

METHOD FOR SYNTHESIZING RADIOACTIVE LIGAND HAVING $^{18}$F-LABELED FLUOROBENZENE RING

TECHNICAL FIELD

The present invention relates to a practical method for synthesizing a radioactive ligand having a $^{18}$F-labeled fluorobenzene ring.

BACKGROUND ART

To the present time, in the production of a radioactive ligand having a $^{18}$F-labeled fluorobenzene ring, an electrophilic substitution reaction or a nucleophilic substitution reaction has been used.

In the electrophilic substitution reaction, a phenyltin derivative has been used as a labeling material. And $^{18}$F fluorine gas has been used as a fluorine reagent. The electrophilic substitution reaction, however, has a disadvantage in that the labeling efficiency and the reaction yield are low. Furthermore, the specific activity, which is an important factor in radiopharmaceuticals, of the compound obtained by this substitution reaction is only a few mCi/μmol.

To overcome this disadvantage, a nucleophilic substitution reaction of a benzene ring by $^{18}$F has often been used. In the nucleophilic substitution reaction, as compared with an electrophilic substitution reaction, the reaction yield is high and the obtained compound is expected to have a high level of specific activity.

However, the most noticeable characteristic of the nucleophilic substitution reaction is that the presence or absence of substituents on a benzene ring or the position and kind of the substituents has an effect not only on the yield of the reaction, but also on the progress of the reaction. Specifically, the nucleophilic substitution reaction requires an electron-withdrawing substituent (e.g., $NO_2$, CN, CHO, COOMe, or COOH) at the para- or ortho-position of the benzene ring. It also requires $NO_2$, Cl, Br, I, $+NMe_3$ or the like as a leaving group. Thus, the production, utilizing the nucleophilic substitution, of a radioactive ligand having a fluorobenzene ring places severe requirements on the substrate, and therefore, lacks general usability.

In such circumstances, the present inventors thought of an idea that the reaction of a diphenyliodonium salt with [$^{18}$F]F$^-$ could be used to synthesize a radioactive ligand having a $^{18}$F-labeled fluorobenzene ring.

There have been reported various methods for synthesizing a diphenyliodonium salt as a labeled precursor. However, in any one of the methods, the synthesis must be carried out under severe conditions, for example, using an oxidant. Thus, it is difficult to synthesize a diphenyliodonium salt, which is expected to be used for various radioactive ligands having complex structures, by any one of the conventional methods. To the present time, in fact, there had been reported no radioactive ligand which was synthesized utilizing the reaction of a diphenyliodonium salt with [$^{18}$F]F$^-$ except for the synthesis of only simple (substituents: H, Me, Cl, OMe, etc.) [$^{18}$F] fluorobenzene derivatives.

A method for producing hydroxy(tosyloxy)iodobenzene is described in Non-Patent Document 1. A method for producing diaryliodonium triflates is described in Non-Patent Document 2. And the reaction of diaryliodonium triflate with [$^{18}$F]F$^-$ is described in Non-Patent Document 3.

Non-Patent Document 1: G. F. Koser et al., J. Org. Chem., 42, 1476 (1977)

Non-Patent Document 2: T. Kitamura et al., Synthesis, 147 (1994)

Non-Patent Document 3: V. W. Pike et al., J. Chem. Soc. Chem. Commun., 2215 (1995)

DISCLOSURE OF THE INVENTION

Problems to be Solved by the Invention

Accordingly, it is an object of the present invention to provide a practical method for synthesizing a radioactive ligand having a $^{18}$F-labeled fluorobenzene ring with various substituents at different positions, which utilizes the nucleophilic substitution of a diphenyliodonium salt with [$^{18}$F]F$^-$ as well as radioactive pharmaceuticals.

Means for Solving the Problems

As described above, generally, compounds used as a $^{18}$F-labeled ligand are chemically unstable and often lose their physiological or pharmacological activity under severe reaction conditions. In the conventional synthetic methods, one benzene ring, which is to be a labeled ligand, is exposed to severe reaction with peracetic acid or the like and then the resultant benzene ring is reacted with the other benzene compound, which is to be a leaving group. Conversely, in the method of the present invention, one benzene ring, which is to undergo elimination reaction, is exposed to severe reaction and the resultant benzene ring is allowed to react with the other benzene ring, which is to be a labeled ligand, under mild conditions; therefore, the method is applicable to relatively unstable ligands.

The present invention provides a method for synthesizing a radioactive ligand having a $^{18}$F-labeled fluorobenzene ring of general formula (7), comprising the steps of:

(A) reacting a phenylhalide compound of general formula (1)

[Formula 1]

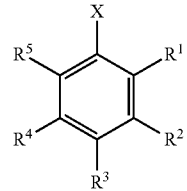

(1)

wherein X is Br or I; $R^1$, $R^2$, $R^3$, $R^4$ and $R^5$ may be the same or different and each represent a hydrogen atom, an alkyl group or a heteroatom-containing functional group, provided that all of $R^1$, $R^2$, $R^3$, $R^4$ and $R^5$ are not a hydrogen atom or an alkyl group, with magnesium metal to produce a Grignard reagent and then treating the Grignard reagent with tin chloride, or reacting the phenylhalide compound with a trialkyltin of general formula (2)

[Formula 2]

$$Sn(R^{10})_3 \quad (2)$$

wherein $R^{10}$ represents an alkyl group in the presence of a palladium catalyst to obtain a phenyltin compound of general formula (3)

[Formula 3]

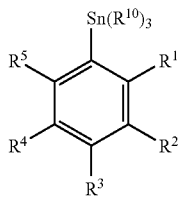
(3)

wherein X, R¹R², R³, R⁴, R⁵ and R¹⁰ are as defined above;

(B) oxidizing an iodobenzene compound of general formula (4)

[Formula 4]

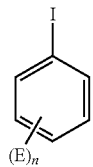
(4)

wherein E represents a functional group which donates electron to a π electron system, and n is 1, 2, 3, 4 or 5, and then reacting the oxidized compound with toluenesulfonic acid monohydrate to obtain a hydroxytosyliodobenzene compound of general formula (5)

[Formula 5]

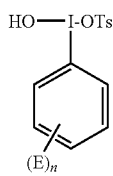
(5)

wherein Ts represents a toluenesulfonyl group; and E and n are as defined above;

(C) reacting the hydroxytosyliodobenzene compound of general formula (5) with the phenyltin compound of general formula (3) to obtain a diphenyliodonium salt of general formula (6)

[Formula 6]

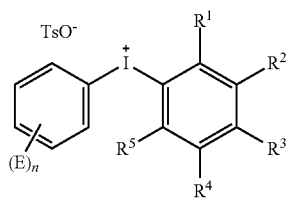
(6)

wherein R¹, R², R³, R⁴, R⁵, E, n and Ts are as defined above; and (D) reacting the diphenyliodonium salt of general formula (6) with [¹⁸F]F⁻ to obtain a radioactive ligand having a ¹⁸F-labeled fluorobenzene ring of general formula (7)

[Formula 7]

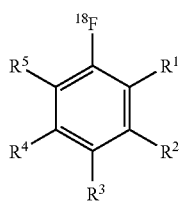
(7)

wherein R¹, R², R³, R⁴ and R⁵ are as defined above.

The present invention also provides a method for obtaining a hydroxytosyliodobenzene compound of general formula (5)

[Formula 9]

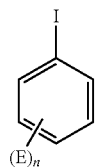
(5)

wherein Ts represents a toluenesulfonyl group; and E and n are as defined above, by oxidizing an iodobenzene compound of general formula (4)

[Formula 8]

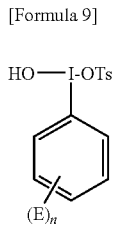
(4)

wherein E represents a functional group which donates electron to a π electron system, and n is 1, 2, 3, 4 or 5, and then reacting the oxidized compound with toluenesulfonic acid monohydrate.

The present invention also provides a hydroxytosyliodobenzene compound of general formula (5)

[Formula 10]

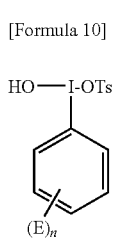
(5)

wherein Ts represents a toluenesulfonyl group; and E represents a functional group which donates electron to a π electron system, and n is 1, 2, 3, 4 or 5.

In the following the present invention will be described in detail.

Step A

Step (A) is a step of reacting a phenylhalide compound of general formula (1)

[Formula 11]

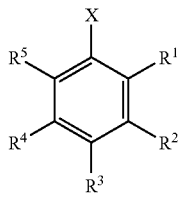
(1)

wherein X is Br or I; $R^1$, $R^2$, $R^3$, $R^4$ and $R^5$ may be the same or different and each represent a hydrogen atom, an alkyl group or a heteroatom containing functional group, provided that all of $R^1$, $R^2$, $R^3$, $R^4$ and $R^5$ are not a hydrogen atom or an alkyl group, with magnesium metal to produce a Grignard reagent and treating the Grignard reagent with tin chloride, or reacting the phenylhalide compound with trialkyltin of general formula (2)

[Formula 12]

$$Sn(R^{10})_3 \qquad (2)$$

wherein $R^{10}$ represents an alkyl group, in the presence of a palladium catalyst to obtain a phenyltin compound of general formula (3)

[Formula 13]

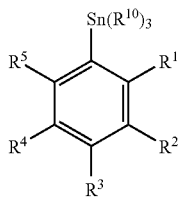
(3)

wherein X, $R^1$, $R^2$, $R^3$, $R^4$, $R^5$ and $R^{10}$ are as defined above.

X is Br or I and preferably Br.

$R^1$, $R^2$, $R^3$, $R^4$ and $R^5$ may be the same or different and each represent a hydrogen atom, an alkyl group, or a heteroatom containing functional group, provided that all of $R^1$, $R^2$, $R^3$, $R^4$ and $R^5$ are not a hydrogen atom or an alkyl group.

"Heteroatom" used in organic chemistry means an atom other than a carbon atom or a hydrogen atom and generally means O, N, S and halogen atoms.

"Halogen atom" means F, Cl, Br and I atoms and preferably a F or Cl atom.

"Alkyl group" herein used means a $C_{1-6}$ alkyl group such as methyl, ethyl, n-propyl, isopropyl, n-butyl, isobutyl, tert-butyl, pentyl or hexyl group.

"Heteroatom-containing functional group" means an amino group, an aminoalkyl group, a carbonylalkyl group, an acyl group, an acyloxy group, a carbonyl group, an alkylcarbonyl group, an alkylcarbonylalkyl group, an arylamino group, an alkenyloxy group, an alkoxy group, an alkylthio group, a haloalkyl group, an aryloxy group, an aralkoxy group, an aralkylthio group, an alkylenedioxy group, an acyl group, an aroyl group, an alkylsulfonyl group, an aralkylsulfonyl group, an arylsulfonyl group, an arylsulfonylamino group, an alkylsulfonylamino group, a dialkylamino group, an ammonio group, a heterocyclic group and a heterocyclic-carbonyl group.

Examples of the aminoalkyl group include an amino-$C_{1-6}$ alkyl group. Examples of the alkylaminoalkyl group include a $C_{1-6}$ alkylamino-$C_{1-6}$ alkyl group. Examples of the carbonylalkyl group include a carbonyl $C_{1-6}$ alkyl group. Examples of the acyl group include a $C_{1-4}$ acyl group such as a formyl or acetyl group. Examples of the alkylcarbonyl group include a $C_{1-6}$ alkylcarbonyl group such as methylcarbonyl and ethylcarbonyl groups. Examples of the alkylcarbonylalkyl group include a $C_{1-6}$ alkylcarbonyl $C_{1-6}$ alkyl group. Examples of the arylamino group include phenylamino, naphthylamino, benzylamino, indanylamino and indenylamino groups. Examples of the alkenyloxy group include a $C_{2-6}$ alkenyl-O— group. Examples of the alkoxy group include a $C_{1-6}$ alkyl-O— group. Examples of the alkylthio group include a $C_{1-6}$ alkyl-S- group. Examples of the haloalkyl group include a halogen-$C_{1-6}$ alkyl group. Examples of the aryloxy group include phenoxy, naphthyloxy, benzyloxy, indanyloxy and indenyloxy groups. Examples of the aralkoxy group include a phenyl-$C_{1-4}$ alkyl-O— group, a naphthyl-$C_{1-4}$ alkyl-O— group, a benzyl-$C_{1-4}$ alkyl-O— group, an indanyl-$C_{1-4}$ alkyl-O— group, and an indenyl-$C_{1-4}$ alkyl-O— group. Examples of the aralkylthio group include a phenyl-$C_{1-4}$ alkyl-S— group, a naphthyl-$C_{1-4}$ alkyl-S— group, a benzyl-$C_{1-4}$ alkyl-S— group, an indanyl-$C_{1-4}$ alkyl-S— group, and an indenyl-$C_{1-4}$ alkyl-S— group. Examples of the alkylenedioxy group include a $C_{1-4}$ alkylenedioxy group such as methylenedioxy and ethylenedioxy groups. Examples of the acyl group include a $C_{1-6}$ acyl group such as a formyl, acetyl or butyryl group. Examples of the aroyl group include a phenyl-CO— group, a naphthyl-CO— group, a benzyl-CO— group, an indanyl-CO— group, and an indenyl-CO— group. Examples of the alkylsulfonyl group include a $C_{1-6}$ alkyl-$SO_2$— group. Examples of the aralkylsulfonyl group include a phenyl-$C_{1-6}$ alkyl-$SO_2$— group, a naphthyl-$C_{1-6}$ alkyl-$SO_2$— group, a benzyl-$C_{1-4}$ alkyl-$SO_2$— group, an indanyl-$C_{1-6}$ alkyl-$SO_2$— group, and an indenyl-$C_{1-6}$ alkyl-$SO_2$— group. Examples of the arylsulfonyl group include a phenyl-$SO_2$— group, a naphthyl-$SO_2$— group, a benzyl-$SO_2$— group, an indanyl-$SO_2$— group, and an indenyl-$SO_2$— group. Examples of the arylsulfonylamino group include a phenyl-$SO_2NH$— group, a naphthyl-$SO_2NH$— group, a benzyl-$SO_2NH$— group, an indanyl-$SO_2NH$— group, and an indenyl-$SO_2NH$— group. Examples of the alkylsulfonylamino group include a $C_{1-6}$ alkyl-$SO_2NH$— group. Examples of the dialkylamino group include a $(C_{1-6}$ alkyl$)_2$N— group such as dimethylamino and diethylamino groups. Examples of the ammonio group include a trialkylammonio group such as trimethylammonio and triethylammonio groups.

Examples of the heterocyclic group include: a 5- or 6-membered ring, fused ring, or bridged ring heterocyclic group which contain, as one or more heteroatoms that form the ring(s), one or more nitrogen atoms and optionally further contain one or more oxygen atoms or sulfur atoms, such as a nitrogen-containing heterocyclic group, such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and a 5- or 6-membered ring, fused ring, or bridged ring heterocyclic group which contain, as one or more heteroatoms that form the ring(s), one or more heteroatoms selected from the group consisting of nitrogen, oxygen and sulfur atoms and optionally contain one or more oxygen atoms or sulfur atoms, such as furyl, thienyl, benzothienyl, pyranyl, isobenzofuranyl, oxazolyl, benzofuranyl, indolyl, benzimidazolyl, benzoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isooxazolyl, thiadiazolyl, oxadiazolyl, pyridazinyl, isoindolyl and isoquinolyl groups.

"Heterocycliccarbonyl group" means a heterocyclic-CO— group.

The groups described so far may have a substituent such as an amino group, a $C_{1-6}$ alkylamino group, a carbonyl group, a $C_{1-6}$ alkoxy group and a $C_{1-6}$ alkylcarbonyl group.

The most preferred compounds of general formula (1) are a compound wherein $R^2$ is —$NR^6(C=O)R^7$, $R^6$ is a 2,5-dimethoxybenzyl group, $R^7$ is a methyl group, $R^3$ is a phenoxy group, and $R^1$, $R^4$ and $R^5$ are a hydrogen atom, as well as a compound wherein $R^1$ is —$CH_2CH(NHR)COOR$, $R^3$ and $R^4$ are —OR or —OCOR, R is a $C_{1-6}$ alkyl group such as a methyl, ethyl, n-propyl, isopropyl, n-butyl, isobutyl, tert-butyl, pentyl or hexyl group, and $R^2$ and $R^5$ are a hydrogen atom.

In general formula (2), $R^{10}$ represents an alkyl group.

Examples of the alkyl group include methyl, ethyl, n-propyl, isopropyl, n-butyl, isobutyl, tert-butyl, pentyl and hexyl groups. Preferably, $R^{10}$ is a $C_{1-6}$ alkyl group and more preferably an n-butyl group.

This step can be carried out by any one of the methods commonly used in reactions in organic synthesis.

Step B

Step (B) is a step of oxidizing an iodobenzene compound of general formula (4)

[Formula 14]

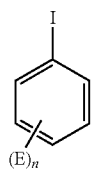

(4)

wherein E represents a functional group which donates electron to a π electron system, and n is 1, 2, 3, 4 or 5, and then reacting the oxidized compound with toluenesulfonic acid monohydrate to obtain a hydroxytosyliodobenzene compound of general formula (5)

[Formula 15]

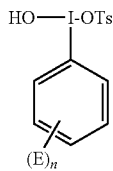

(5)

wherein Ts represents a toluenesulfonyl group; and E and n are as defined above.

Examples of the functional groups which donate electron to a π electron system include —$NR_2$, —OR, —NHCOR, —$NHSO_2R$, —OCOR, —SR, and —R (R is a hydrogen atom or an alkyl group with 1 to 6 carbon atoms). n is 1, 2, 3, 4 or 5 and preferably 2 or larger. In the case that n is 2 or larger, n quantities of Es may be the same or different. Examples of the preferable hydroxytosyliodobenzene compounds include one in which n=1, one quantity of E is a methoxy group and is substituted at the para-position, relative to I, of the benzene ring; and one in which n=2, 2 quantities of Es are both a methoxy group and are substituted at the meta- and para-positions, relative to I, of the benzene ring.

This step can be carried out by any one of the commonly used methods, such as the method described in literature (G. F. Koser et al., J. Org. Chem., 42, 1476 (1977)). For example, an iodobenzene compound of general formula (4) is reacted with peracetic acid or sodium borate (in acetic acid) to from a periodine compound, and the periodine compound is treated with acetonitrile and tosic acid monohydrate in ether at room temperature. In the case that hydroxyiodobenzene having an electron-donating group is so unstable that it decomposes in air, a technique such as 1) carrying out all reactions in a nitrogen atmosphere or 2) carrying out a series of reactions without isolating the intermediates, can be used.

Step C

Step (C) is a step of reacting the hydroxytosyliodobenzene compound of general formula (5) with the phenyltin compound of general formula (3) to obtain a diphenyliodonium salt of general formula (6)

[Formula 16]

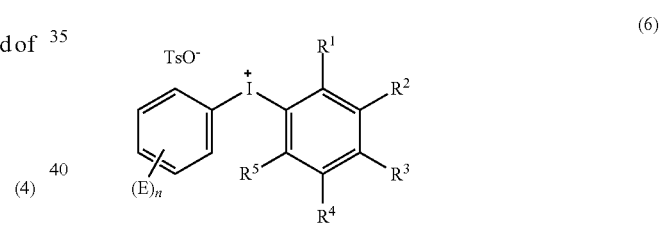

(6)

wherein $R^1$, $R^2$, $R^3$, $R^4$, $R^5$, E, n and Ts are as defined above.

This step can be carried out by any one of the methods and under conditions commonly used in the reaction of a hydroxytosyliodobenzene compound with a phenyltin compound.

Step D

Step (D) is a step of reacting the diphenyliodonium salt of general formula (6) with [$^{18}$F]F$^-$ to obtain a radioactive ligand having a $^{18}$F-labeled fluorobenzene ring of general formula (7)

[Formula 17]

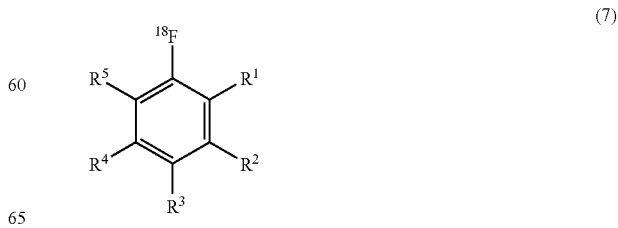

(7)

wherein $R^1$, $R^2$, $R^3$, $R^4$ and $R^5$ are as defined above.

This step can be carried out by any one of the commonly used methods, such as the method described in literature (V. W. Pike et al., J. Chem. Soc. Chem. Commun., 2215 (1995)).

For example, heating the diphenyliodonium salt of general formula (6) together with [$^{18}$F]F$^-$ in an appropriate solvent (e.g. THF, DMF, DMSO, HMPA, Sulfone) for 0 to 30 minutes gives [$^{18}$F]PhF in a yield of about 50%. Carrying out the reaction under microwave irradiation using DMSO as a reaction solvent allows the yield of [$^{18}$F]PhF to reach 80% or more even if the reaction time is as short as 5 minutes (n>5).

The radioactive ligand having a $^{18}$F-labeled fluorobenzene ring thus obtained has a useful physiological or pharmacological activity, and its use for elucidation of the biofunctions is expected.

Advantages of the Invention

The use of the synthetic method of the present invention can provide radioactive ligands having various substituents and physiological or pharmacological activity. The present inventors contemplate using this labeling method in the production of a radioactive ligand having an $^{18}$F-labeled fluorobenzene ring. This method can be used particularly in the synthesis of [$^{18}$F]FDOPA, [$^{18}$F]DAA1106, [$^{18}$F]Spiperone, [$^{18}$F]Ketaserine, [$^{18}$F]Flumazenil, [$^{18}$F]Resperidone and the like. Moreover, the method offers such advantages that a series of the reactions is carried out under mild conditions and the product is obtained in a high yield in a short period of time.

EXAMPLE

For better understanding, the present invention will be described in more detail by an example. Needless to say, the present invention is not intended to be limited to this example.

Example 1

Production of (2,5-dimethoxybenzyl)-N-(5-($^{18}$F) fluoro-2-phenoxyphenyl)acetamide (hereinafter referred to as [$^{18}$F]DAA1106)

1-1) N-(2,5-dimethoxybenzyl)-N-(5-bromo-2-phenoxyphenyl)acetamide (510 mg, 1.12 mmol) was dissolved in toluene, hexabutyltin (IV) and dichlorobis(triphenylphosphine)palladium (0) were added and the mixture was circulated for 4 days. After toluene was removed, the reaction product was purified by silica gel column chromatography (eluent: hexane/ethyl acetate=1:4) to obtain 320 mg (43%) of N-(2,5-dimethoxybenzyl)-N-(5-tributylstannyl-2-phenoxyphenyl)acetamide.

FABMS $C_{36}H_{48}FNO_3Sn$(m/z) 680.5 (m$^+$+1).

4-Methoxyiodobenzene diacetate (350 mg, 1 mmol) was suspended in CH$_3$CN (5 mL), and tosic acid monohydrate (172 mg, 1 mmol) was added dropwise under ice cooling.

After addition of tosic acid monohydrate was completed and the color of the reaction solution was changed from colorless to yellow due to the dissolution of diacetate in the reaction solution, the solution of the tin compound (681 mg, 1 mmol) in CH$_3$CN (1 mL) was added dropwise thereto. The reaction solution was stirred at room temperature for 2 hours and CH$_3$CN was removed. The residue was crystallized using a solvent such as ether, hexane and the like to obtain a diphenyliodonium salt compound. All the operations so far were performed under a nitrogen atmosphere.

The above diphenyliodonium salt compound (5 mg) was dissolved in DMSO (200 ml), [$^{18}$F]KF (5 mCi)/Kryptofix was introduced thereinto and the resultant solution was heated at 80° C. for 20 minutes. After completion of the reaction, the reaction mixture was injected into reversed-phase semi-separation HPLC (YMC J' sphere ODS-H80 column, 10 mmID× 250 mm). The fraction of [$^{18}$F]DAA1106 was collected using CH$_3$CN/H$_2$O (6/4) as the mobile phase at a flow late of 6 mL/min. From the fraction, the solvent was removed under reduced pressure, and the resultant fraction was dissolved in physiological saline (1 mL) and passed through a 0.22-m millipore filter to obtain [$^{18}$F]DAA1106 (1.3 mCi, specific activity: 4.5 Ci/µmol, radiochemical purity: 99%).

The invention claimed is:
1. A method for synthesizing a radioactive ligand having a $^{18}$F-labeled fluorobenzene ring of general formula (7), comprising the steps of:
  (A) reacting a phenylhalide compound of general formula (1)

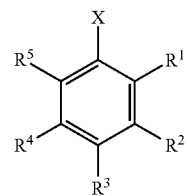

(1)

wherein X is Br or I; R$^1$, R$^2$, R$^3$, R$^4$ and R$^5$ may be the same or different and each represent a hydrogen atom, an alkyl group or a heteroatom-containing functional group, provided that all of R$^1$, R$^2$, R$^3$, R$^4$ and R$^5$ are not a hydrogen atom or an alkyl group,
  with a trialkyltin of general formula (2)

(2)

wherein R$^{10}$ represents an alkyl group
  in the presence of a palladium catalyst to obtain a phenyltin compound of general formula

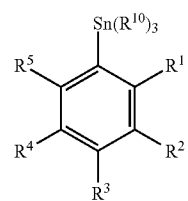

(3)

wherein X, R$^1$, R$^2$, R$^3$, R$^4$, R$^5$ and R$^{10}$ are as defined above;
  (B) oxidizing an iodobenzene compound of general formula (4)

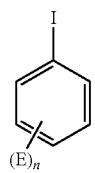

(4)

wherein E represents a functional group which donates electron to a π electron system, and n is 1, 2, 3, 4 or 5, and then reacting the oxidized compound with toluenesulfonic acid monohydrate to obtain a hydroxytosyliodobenzene compound of general formula (5)

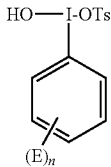

(5)

wherein Ts represents a toluenesulfonyl group; and E and n are as defined above;

(C) reacting the hydroxytosyliodobenzene compound of general formula (5) with the phenyltin compound of general formula (3) to obtain a diphenyliodonium salt of general formula (6)

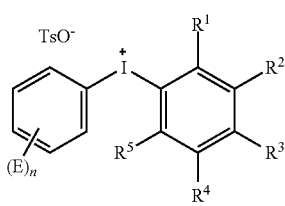

(6)

wherein $R^1$, $R^2$, $R^3$, $R^4$, $R^5$, E, n and Ts are as defined above; and (D) reacting the diphenyliodonium salt of general formula (6) with [$^{18}$F]F$^-$ to obtain a radioactive ligand having a $^{18}$F-labeled fluorobenzene ring of general formula (7)

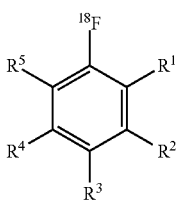

(7)

wherein $R^1$, $R^2$, $R^3$, $R^4$ and $R^5$ are as defined above.

2. A method for obtaining a hydroxytosyliodobenzene compound of general formula (5)

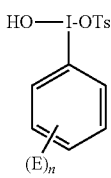

(5)

wherein Ts represents a toluenesulfonyl group; and E and n are as defined below, by oxidizing an iodobenzene compound of general formula (4)

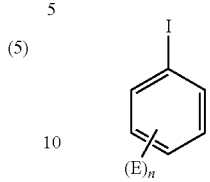

(4)

wherein E represents a functional group which donates electron to a π electron system, and n is 1, 2, 3, 4 or 5, and then reacting the oxidized compound with toluenesulfonic acid monohydrate.

3. The method for synthesizing a radioactive ligand as claimed in claim 1,
wherein $R^2$ is —NR$^6$(C=O)R$^7$, $R^6$ is a 2,5-dimethoxybenzyl group, $R^7$ is a methyl group, $R^3$ is a phenoxy group, and $R^1$, $R^4$ and $R^5$ are each a hydrogen atom.

4. The method for synthesizing a radioactive ligand as claimed in claim 1,
wherein $R^1$ is —CH$_2$CH(NHR)COOR, $R^3$ and $R^4$ are —OR or —OCOR, R is a C$_{1-6}$ alkyl group, and $R^2$ and $R^5$ are each a hydrogen atom.

5. The method for synthesizing a radioactive ligand as claimed in claim 4,
wherein R is selected from the group consisting of methyl, ethyl, n-propyl, isopropyl, n-butyl, isobutyl, tert-butyl, pentyl and hexyl group.

6. The method for synthesizing a radioactive ligand as claimed in claim 1,
wherein E is selected from the group consisting of —NR$_2$, —OR, —NHCOR, —NHSO$_2$R, —OCOR, —SR, and —R, wherein R is a hydrogen atom or a C$_{1-6}$ alkyl group.

7. The method for synthesizing a radioactive ligand as claimed in claim 2,
wherein E is selected from the group consisting of —NR$_2$, —OR, —NHCOR, —NHSO$_2$R, —OCOR, —SR, and —R, wherein R is a hydrogen atom or a C$_{1-6}$ alkyl group.

8. The method for synthesizing a radioactive ligand as claimed in claim 1,
wherein when n is 2, 3, 4 or 5, n quantities of E may be the same or different.

9. The method for synthesizing a radioactive ligand as claimed in claim 2,
wherein when n is 2, 3, 4 or 5, n quantities of E may be the same or different.

10. The method for synthesizing a radioactive ligand as claimed in claim 1,
wherein n=1, and 1 quantity of E is a methoxy group and is substituted at the para-position, relative to I of the benzene ring.

11. The method for synthesizing a radioactive ligand as claimed in claim 2,
wherein n=1, and 1 quantity of E is a methoxy group and is substituted at the para-position, relative to I of the benzene ring.

12. The method for synthesizing a radioactive ligand as claimed in claim 8,
wherein n=2, and 2 quantities of E are both a methoxy group and are substituted at the meta- and para-positions, relative to I of the benzene ring.

13. The method for synthesizing a radioactive ligand as claimed in claim 9,
wherein n=2, and 2 quantities of E are both a methoxy group and are substituted at the meta- and para-positions, relative to I of the benzene ring.

14. The method for synthesizing a radioactive ligand as claimed in claim 1,
wherein in step (B) the oxidized compound is a periodine compound, and wherein the iodobenzene compound of general formula (4)

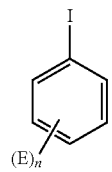

(4)

is oxidized by reacting with peracetic acid or sodium borate in acetic acid to form the periodine compound.

* * * * *